United States Patent [19]

Laurenzo et al.

[11] Patent Number: 4,942,260

[45] Date of Patent: Jul. 17, 1990

[54] AMINE OXIDE PROCESS WITH $CO_2$ AND ALUMINUM

[75] Inventors: Kathleen S. Laurenzo; Joe D. Sauer, both of Baton Rouge, La.

[73] Assignee: Ethyl Corporation, Richmond, Va.

[21] Appl. No.: 237,098

[22] Filed: Aug. 29, 1988

[51] Int. Cl.$^5$ ............................................ C07C 135/02
[52] U.S. Cl. .................................... 564/298; 544/173; 544/383; 546/184; 546/347; 564/299
[58] Field of Search ............... 564/298, 112, 184, 347; 260/689; 544/173, 383

[56]  References Cited

U.S. PATENT DOCUMENTS 4,247,480  1/1981  Murata et al.

OTHER PUBLICATIONS

Lunn and Sansone "Reductive Destruction of N-Nitrosodimethylamine ... " Fd Cosmet. Toxicol. vol. 19 pp. 493-494 (1981).

Primary Examiner—Glennon H. Hollrah
Assistant Examiner—Scott C. Rand
Attorney, Agent, or Firm—Joseph D. Odenweller

[57]  ABSTRACT

Amine oxides which have low levels of nitrosamines or are substantially-free of nitrosamines are made by reacting tert-amines with hydrogen peroxide in the presence of carbon dioxide and aluminum metal.

11 Claims, No Drawings

AMINE OXIDE PROCESS WITH $CO_2$ AND ALUMINUM

BACKGROUND OF THE INVENTION

It is known to make tert-amine oxides by the reaction of aqueous hydrogen peroxides with tert-amines. This reaction can also be conducted using a co-solvent such as a lower alcohol to prevent gel formation.

Murata et al. U.S. Pat. No. 4,247,480 discloses that the formation of amine oxides from tert-amine by reaction with hydrogen peroxide can be promoted by including 0.01–2 weight percent carbon dioxide based on the tert-amine. Murata et al. demonstrates the process at 55°–65° C. and obtains excellent yields of amine oxides.

It is known that nitrosamine impurities are routinely formed when reacting hydrogen peroxide with tert-amines. This would not be a problem if it were not for the fact that nitrosamines are suspected carcinogens and mutagens and even small amounts cannot be tolerated in products intended for contact with humans, "Nitrosamines: Assessing the Relative Risk" Chemical & Engineering News, pages 20–26, Mar. 31, 1980. The major uses for tert-amine oxides are in cosmetic and surfactant formulations including such things as laundry detergents, hair shampoo and hair conditioners, all of which come in contact with humans. This necessitates special procedures to remove nitrosamine impurities from tert-amine oxides before they can be used in their major marketing areas. Such treatments include the exposure of the tert-amine oxide to ultra-violet irradiation (anonymous GB RD 269056A). Therefore a need exists for a process for making tert-amine oxides that have low concentrations or are substantially free of nitrosamine impurities without resorting to any special purification procedure after the synthesis operation.

SUMMARY OF THE INVENTION

It has now been discovered that amine oxides that have low levels of nitrosamines or are substantially nitrosamine-free can be readily made by reacting a tert-amine with aqueous hydrogen peroxide in the presence of added carbon dioxide and aluminum metal.

DESCRIPTION OF THE PREFERRED EMBODIMENTS

A preferred embodiment of the invention is a process for making a low nitrosamine or substantially nitrosamine-free amine oxide, said process comprising reacting a tertiary amine with aqueous hydrogen peroxide in the presence of a catalyst formed by adding carbon dioxide to the reaction mixture and in contact with aluminum metal.

By "low nitrosamine" is meant a nitrosamine content below 200 ppb and more preferably below 100 ppb. Following this embodiment of the invention has resulted in nitrosamine concentrations which are below the level of detection by the Thermal Energy Analyzer procedure substantially as described by Krull et al., Anal. Chem. 51 1706 (1979).

The process is applicable to any of a broad range of tert-amines such as butyldimethylamine, hexyldimethylamine, isobutyldimethylamine, 2-ethylhexyldimethylamine, octyldimethylamine, decyldimethylamine, dodecyldimethylamine, tetradecyldimethylamine, hexadecyldimethylamine, eicosyldimethylamine, docosyldimethylamine, triacontyldimethylamine, tributylamine, butyldiethylamine, isobutyldiethylamine, decylbutylethylamine, hexadecylhexylmethylamine, eicosyldibutylamine, trioctylamine, tridodecylamine, dieicosylethylamine, ditriacontylmethylamine, N,N,-dimethyl-aniline, N-methyl-N-dodecylaniline, cyclopentyldimethylamine, cyclohexyldimethylamine, dicyclohexylmethylamine, cyclododecyldimethylamine, diphenylbutylamine, para-tolyldiethylamine, α-naphthylbutylmethylamine, benzylbutylmethylamine, α-methylbenzylbutylmethylamine, (4-butylbenzyl)octylmethylamine, dibenzylbutylamine, 4-pentylbenzyldibutylamine, N-butylmorpholine, N-methylmorpholine, N-methylpiperidine, N-dodecylpiperidine, N-octadecylpiperidine, N-triacontylpiperidine, N-methylpiperazine, N-butylpiperazine, N-octylpiperazine, N-phenylpiperidine, N-benzylpiperidine, N-cyclohexylpiperidine, pyridine and the like.

In a more preferred embodiment the tert-amine is a primary trialkylamine having the structure $R^1R^2R^3N$ wherein $R^1$, $R^2$ and $R^3$ are primary alkyls having 1–30 carbon atoms. Representative examples of these include but are not limited to trimethylamine, tri-n-pentylamine, tri-n-dodecylamine, n-octa decyl-di-(n-butyl)amine, n-eicosyl-di-(n-decyl)amine, n-triacontyl, n-dodecyl methylamine and the like.

In a still more preferred embodiment $R^1$ is a primary alkyl group containing 6–20 carbon atoms and $R^2$ and $R^3$ are independently selected from methyl and ethyl groups.

In a further preferred embodiment $R^1$ is a mainly linear primary alkyl containing 8–20 carbon atoms and $R^2$ and $R^3$ are methyl groups. By "mainly linear" is meant that over 50 percent, more preferably 70 percent and most preferably 90 percent of the $R^1$ groups are linear alkyls containing 8–20 carbon atoms.

Examples of these preferred embodiments are octyldimethylamine, decyldimethylamine, dodecyldimethylamine, tetradecyldimethylamine, hexadecyldimethylamine, octadecyldimethylamine, eicosyldimethylamine and mixtures thereof.

In another more preferred embodiment of the invention, both $R^1$ and $R^2$ are independently selected from primary alkyls containing 6–20 carbon atoms and $R^3$ is a methyl or ethyl group.

In a highly preferred embodiment $R^1$ and $R^2$ are independently selected from mainly linear primary alkyl groups containing 8–20 carbon atoms and $R^3$ is methyl. Examples of this highly preferred embodiment are dioctylmethylamine, didecylmethylamine, didodecylmethylamine, ditetradecylmethylamine, dihexadecylmethylamine, dioctadecylmethylamine, dieicosylmethylamine, decyloctylmethylamine, dodecyloctylmethylamine, tetradecyldecylmethylamine, hexadecyltetradecylmethylamine, octadecylhexadecylmethylamine, eicosyldodecylmethylamine and the like including mixtures thereof.

Any aqueous hydrogen peroxide can be used including those containing 3–100 percent $H_2O_2$. Preferably the hydrogen peroxide is 20–70 weight percent active $H_2O_2$. When the tert-amine is linear $C_{8-20}$ alkyl dimethylamine, it is preferred that the aqueous hydrogen peroxide be about 20–40 weight percent $H_2O_2$ to avoid gel formation. Alternatively, more concentrated hydrogen peroxide can be used and additional water either added initially or co-fed to maintain a stirrable reaction mixture. In this mode of operation it is the "net" $H_2O_2$ concentration, taking into account the additional water, that controls gel and should be kept in a gel-free range.

For example, co-feeding 100 g of 50 percent aqueous hydrogen peroxide and 100 g of water gives a "net" 25 percent aqueous hydrogen peroxide. Likewise prior addition of 100 g of water to the tert-amine followed by feeding 100 grams of 50 percent aqueous hydrogen peroxide gives a "net" 25 percent aqueous hydrogen peroxide. Likewise, co-solvents such as lower alcohol, e.g., isopropanol, isobutanol and the like, can be used to avoid gelation.

The amount of hydrogen peroxide should be at least a stoichiometric amount. A useful range is about 1–5 moles of $H_2O_2$ and more preferably 1–1.5 mole of $H_2O_2$ per mole of tert-amine. A highly preferred amount is about 1.0–1.3 moles of $H_2O_2$ and especially about 1.05–1.2 moles of $H_2O_2$ per mole of tert-amine. Any substantial amount of unreacted $H_2O_2$ remaining after the reaction can be destroyed by the addition of a reducing agent or a peroxide decomposition catalyst.

When the process is conducted using a di-linear alkyl methylamine, the process can be carried out using more concentrated aqueous hydrogen peroxide such as about 45–70 weight percent hydrogen peroxide. When the di-linear alkyls contain about 6–12 carbon atoms each, the reaction mixture will remain substantially gel free. When the di-linear alkyls contain 14 or more carbon atoms the reaction mixture will set up to a dry flakeable solid on cooling.

The reaction must be conducted using added carbon dioxide. The reaction can be pressurized (e.g., to 5–500 psig or higher) with carbon dioxide or merely provided with a carbon dioxide blanket. An effective way to conduct the reaction is to sparge carbon dioxide into the reaction liquid phase or to maintain a carbon dioxide sweep over the liquid reaction phase during all or a portion of the reaction. If the reaction rate slows down towards the end of the reaction, additional carbon dioxide can be injected.

The amount of carbon dioxide added should be an amount which catalyzes the reaction causing it to proceed at a faster rate. This can range from about 0.005 weight percent up to the solubility limit of the carbon dioxide in the tert-amine. A more preferred range is 0.01 weight percent up to the solubility limit of carbon dioxide in the system at the reaction temperature.

The reaction can be conducted at any temperature high enough to cause the desired reaction to proceed but not so high as to cause decomposition. A useful temperature range is about 10°–100° C. more preferably 20°–80° C. The reaction proceeds faster at higher temperature so it is preferred to conduct the process at as high a temperature as is possible as long as the nitrosamine level stays below the desired limit. If nitrosamines start nitrosamine formation is brought to or below the desired maximum. Temperatures below 40° C. usually result in very low levels of nitrosamines.

In one mode of operation the aqueous hydrogen peroxide feed to the tert-amine is started at a low temperature, preferably below 40° C., and continued below 40° C. until at least 20 weight percent of the stoichiometric amount of hydrogen peroxide has been reacted. The temperature is then permitted to gradually increase above 40° C. during the remainder of the hydrogen peroxide feed as long as it stays below 70° C. If at the end of the hydrogen peroxide feed the reaction temperature is below about 55° C., the conversion of the remaining tert-amine to amine oxide can be accelerated by heating the mixture to about 65° C. for a period of about 0.5–2 hours.

The reaction time is a variable and depends on the tert-amine selected, the reaction temperature and the reaction scale. Generally, the reaction is complete in about 1–24 hours, more often in about 2–12 hours and most often is about 3–8 hours. Progress of the reaction after all of the hydrogen peroxide and tert-amine have been mixed can be followed by withdrawing small samples and analyzing for free amine. The reaction is considered complete when the free amine level drops below about 3 weight percent. At this stage the product may be packaged for use or shipment. Any residual free amine will continue to decrease on standing and/or during packaging or storage prior to shipment until it finally becomes non-detectable.

Contact with aluminum metal can be achieved by conducting the reaction in an aluminum-lined reactor although this is not necessary and would lead to excessive investment. Aluminum metal contact can be achieved at very little additional cost by merely immersing aluminum metal coupons in the reaction liquid phase. Optionally part of the reactor such as the stirrer head could be constructed with aluminum metal. The amount of aluminum metal contact can be easily determined experimentally since it does depend to some extent on the amount of agitation in the reactor. A useful range is about 5–500 cm$^2$ of aluminum surface per liter of reaction liquid volume. A more preferred range is about 10–100 cm$^2$/L. Since the aluminum effect appears to be a surface phenomenon, the total surface area is what counts. A 5 cm x 5 cm coupon has approximately 50 cm$^2$ of surface area.

The process is conducted by placing the tert-amine and any solvent used (e.g. water, alcohol) in a reactor containing the required clean aluminum metal surface. Carbon dioxide is then either sparged into the liquid phase or merely swept across the liquid surface. Optionally, the reactor can be pressurized with carbon dioxide. Then aqueous hydrogen peroxide feed is started while stirring at the desired temperature. After completion of the hydrogen peroxide feed, stirring is continued at reaction temperature until the unreacted tert-amine level drops below about 3 weight percent. The reaction product is then ready for packaging and use.

The following examples show how the reaction is conducted and compare the new process with a reaction carried out in the same manner but without the aluminum metal.

EXAMPLE 1

This is a baseline run without either aluminum or $CO_2$ for comparative purposes.

In a reaction flask was placed 250 g dodecyldimethylamine. Then 84.2 g of 50 percent aqueous hydrogen peroxide was added slowly to the stirred mixture at 60°–67° C. (mostly 63°–67° C.) over a 88-minute period. Water was added periodically to prevent gel (total water 585 g).

| Time From Start | Amine Conversion (%) |
| --- | --- |
| 1.5 hours | 25% |
| 3.5 hours | 72% |
| 7.0 hours | 84% |

A sample taken at 7.0 hours from start analyzed 418 ppb N-nitrosodimethylamine and 321 ppb N-nitrosododecylmethylamine using a Thermal Energy Analyzer as an adaptation of the method described by Krull et al. "Anal. Chem." 51 1706 (1979). The reaction was let stand overnight at room temperature. The mixture was re-heated to 65 with stirring and the reaction was continued.

| Time From Re-Start | Amine Conversion (%) |
| --- | --- |
| 2 hours | 87% |
| 4 hours | 91% |
| 7 hours | 91% |
| 23.5 hours | 91% |

It can be seen that the reaction without catalyst is quite slow. A sample of product taken at 4 hours from restart was analyzed for nitrosamines and found to contain 418 ppb N-nitrosodimethylamine and 296 ppb N-nitrosododecylmethylamine.

EXAMPLE 2

This is an example conducted with the aluminum coupon but without carbon dioxide.

In a glass reaction flask was placed 250 g dodecyldimethylamine. An aluminum coupon (7.62 cm x 1.27 cm x 0.318 cm) was suspended in the liquid phase. The amine was heated to 65° C. and 83.6 g of 50 weight percent aqueous hydrogen peroxide was added over a 70-minute period. Water was added concurrently at such a rate as to just keep the reaction mixture fluid. After 110 minutes, 300 ml of water had been added. The reaction mixture was stirred at 65° C. for an additional 5 hours and 40 minutes at which time analysis by $^1$H NMR showed >96% conversion. The remaining water was then added (for a total of 563 g) and the reaction mixture was cooled to room temperature and analyzed as in Example 1. The analysis showed 534 ppb N-nitrosodimethylamine and 698 ppb N-nitrosododecylmethylamine.

EXAMPLE 3

This is a comparative example conducted with CO2 but without the aluminum coupon.

In a glass reaction flask was placed 250 g dodecyldimethylamine. The amine was heated to 65° C. under a carbon dioxide atmosphere and 86 g of 50 percent aqueous hydrogen peroxide and 584 ml of water were added over a 1-hour period. Stirring was continued for 2 hours at 65° C. Conversion to dodecyldimethylamine oxide was essentially complete. The product was analyzed as in Example 1. The analysis showed 96 ppb N-nitroso dimethylamine.

EXAMPLE 4

This example was conducted with both $CO_2$ and aluminum in the reaction mixture.

In a glass reaction flask was placed 250 g of dodecyl dimethylamine and 563 g of water. An aluminum coupon (7.62 cm x 1.27 cm x 0.318 cm) was suspended in the liquid phase. The flask was swept with carbon dioxide and heated to 65° C. under a carbon dioxide atmosphere. Then 83.6 g of 50 weight percent aqueous hydrogen peroxide was added over a 65-minute period at 65° C. The mixture was then stirred an additional 115 minutes at 65° C. Analysis by $^1$H NMR showed over 99 percent conversion of tert-amine to dodecyldimethylamine oxide. The product was analyzed for N-nitrosodimethylamine and N-nitrosododecylmethylamine as in Example 1. The analysis was conducted by an independent laboratory (Thermedics Incorporated). The limits of detection were 10 ppb N-nitrosodimethylamine and 80 ppb N-nitrosododecylmethylamine. Both nitrosamines were below the limit of detection.

The above results show that by conducting the oxidation in the presence of both carbon dioxide and aluminum metal the nitrosamine level is kept below the limit of detection even when operating at fairly high temperatures. The invention satisfies a long-felt health and environment need.

We claim:

1. A process for making a low nitrosamine or substantially nitrosamine-free amine oxide, said process consisting essentially of reacting a tertiary amine with aqueous hydrogen peroxide in the presence of a catalyst formed by adding carbon dioxide to the reaction mixture and in contact with aluminum metal.

2. The process of claim 1 conducted in a temperature range of 20°–80° C.

3. A process of claim 2 wherein said tertiary amine has the structure $R^1R^2R^3N$ wherein $R^1$ is a primary alkyl group containing 6–20 carbon atoms and $R^2$ and $R^3$ are methyl or ethyl.

4. A process of claim 3 wherein $R^1$ is a primary mainly linear alkyl group containing 8–20 carbon atoms and $R^2$ and $R^3$ are methyl groups.

5. A process of claim 4 wherein $R^1$ is dodecyl.

6. A process of claim 2 wherein said tertiary amine has the structure $R^1R^2R^3N$ wherein $R^1$ and $R^2$ are independently selected from primary alkyl groups containing 6–20 carbon atoms and $R^3$ is methyl or ethyl.

7. A process of claim 6 wherein $R^1$ and $R^2$ are primary mainly linear alkyl groups containing 8–20 carbon atoms and $R^3$ is methyl.

8. A process of claim 7 wherein $R^1$ and $R^2$ are decyl.

9. A process of claim 1 conducted at 20°–40° C.

10. A process of claim 1 conducted at an initial temperature below 40° C. until at least 20 weight percent of the stoichiometric amount of hydrogen peroxide has reacted with said tertiary amine and then allowing the temperature to gradually increase to a temperature above 40° C. and below 70° C.

11. A process of claim 10 conducted at a temperature of about 20°–40° C.

* * * * *